US006925330B2

(12) United States Patent
Kleine

(10) Patent No.: US 6,925,330 B2
(45) Date of Patent: Aug. 2, 2005

(54) IMPLANTABLE MEDICAL DEVICE AND METHOD FOR DETECTING CARDIAC EVENTS WITHOUT USING OF REFRACTORY OR BLANKING PERIODS

(75) Inventor: Bruce Kleine, Reseda, CA (US)

(73) Assignee: Pacesetter, Inc., Sylmar, CA (US)

(*) Notice: Subject to any disclaimer, the term of this patent is extended or adjusted under 35 U.S.C. 154(b) by 433 days.

(21) Appl. No.: 10/193,040

(22) Filed: Jul. 10, 2002

(65) Prior Publication Data

US 2004/0010294 A1 Jan. 15, 2004

(51) Int. Cl.$^7$ .............................................. A61N 1/362
(52) U.S. Cl. ............................ 607/9; 607/26; 600/512
(58) Field of Search .............................. 600/508–509, 600/512; 607/9, 26

(56) References Cited

U.S. PATENT DOCUMENTS

| 4,742,458 A | 5/1988 | Nathans et al. ............. 364/417 |
| 5,522,855 A | 6/1996 | Hoegnelid ..................... 607/9 |
| 5,620,471 A | 4/1997 | Duncan ....................... 607/14 |
| 6,097,983 A | 8/2000 | Standberg et al. ............. 607/9 |
| 6,236,883 B1 | 5/2001 | Ciaccio et al. .............. 600/515 |
| 6,266,554 B1 * | 7/2001 | Hsu et al. .................... 600/515 |
| 6,324,421 B1 | 11/2001 | Stadler et al. .............. 600/509 |
| 6,381,493 B1 | 4/2002 | Stadler et al. ................. 607/9 |
| 6,397,100 B2 | 5/2002 | Stadler et al. .............. 600/509 |
| 6,760,615 B2 * | 7/2004 | Ferek-Petric ................ 600/518 |
| 6,760,622 B2 * | 7/2004 | Helland et al. ................. 607/9 |

2003/0083587 A1 * 5/2003 Ferek-Petric ................ 600/512

FOREIGN PATENT DOCUMENTS

EP          0 570 896 A2 *  5/1993   ........... G06F/15/20

* cited by examiner

Primary Examiner—Carl Layno

(57) ABSTRACT

Cardiac electrical events are detected by comparing signal vectors with pre-determined classification zones representative of different cardiac events. The signal vector is generated by sensing the voltages between various combinations of electrodes, such as A-tip to V-tip, A-tip to A-ring, and A-ring to V-ring. The signal vector is compared with a set of classification zones corresponding to different events, such as P-waves, R-waves, T-waves, A-pulses, and V-pulses, to determine whether the vector lies within any of the classification zones. In this manner, cardiac events are detected using only the voltages received from the electrodes and no refractory periods or blanking periods are required to distinguish one event from another. The classification zones vary from patient to patient and a technique is provided herein for generating a set of vector classification zones for a particular patient. Signal vectors corresponding to various unknown cardiac events are generated by the implanted device and are transmitted to an external device programmer. ECG signals, generated by a surface ECG detector, are simultaneously received by the external programmer. The external programmer identifies the cardiac electrical event corresponding to each signal vector based on the ECG signals and then generates classification zones for each event type using only the signal vectors corresponding to the event.

28 Claims, 12 Drawing Sheets

IMPLANTABLE MEDICAL DEVICE AND METHOD FOR DETECTING CARDIAC EVENTS WITHOUT USING OF REFRACTORY OR BLANKING PERIODS

CROSS-REFERENCE TO RELATED APPLICATIONS

This application is related to copending U.S. patent application Ser. No. 10/139,042, titled "IMPLANTABLE MEDICAL DEVICE AND METHOD FOR DETECTING CARDIAC EVENTS WITHOUT USING OF REFRACTORY OR BLANKING PERIODS," filed concurrently herewith.

FIELD OF THE INVENTION

The invention generally relates to implantable medical devices, such as pacemakers or implantable cardioverter-defibrillators ("ICDs") and, in particular, to techniques for detecting electrical cardiac events using an implantable medical device.

BACKGROUND OF THE INVENTION

A pacemaker is a medical device, typically implanted within a patient, which recognizes various disrythmias such as an abnormally slow heart rate (bradycardia) or an abnormally fast heart rate (tachycardia) and delivers electrical pacing pulses to the heart in an effort to remedy the disrythmias. An ICD is a device, also implantable into a patient, which additionally recognizes atrial fibrillation (AF) or ventricular fibrillation (VF) and delivers electrical shocks to terminate fibrillation.

Pacemakers and ICDs carefully monitor characteristics of the heart such as the heart rate to detect disrythmias, discriminate among different types of disrythmias, identify appropriate therapy, and determine when to administer the therapy. The heart rate, for example, is monitored by examining the electrical signals that are manifest concurrent with the depolarization or contraction of the myocardial tissue of the heart. The electrical signals are detected internally by sensing leads mounted within the heart and are referred to as intracardiac electrogram ("IEGM") signals. The normal contraction of atrial muscle tissue appears as a P-wave within the IEGM. A sequence of consecutive P-waves defines the atrial rate. The normal contraction of ventricular muscle tissue appears as an R-wave (sometimes referred to as the "QRS complex") within the IEGM. A sequence of consecutive R-waves defines the ventricular rate. If the heart is subject to flutter or fibrillation, P-waves and R-waves typically cannot be discerned within the IEGM. Hence, the pacemaker or ICD may need to rely on other characteristics of the IEGM to discriminate among different types of flutter and fibrillation, to identify optimal therapy, and to determine when to administer the therapy. Some state of the art pacemakers and ICDs are capable of sensing electrical signals independently in the atria and in the ventricles. Hence, an atrial IEGM and a separate ventricular IEGM are detected. The atrial rate is determined based upon P-waves detected in the atrial IEGM. The ventricular rate is determined based upon R-waves detected within the ventricular IEGM.

Thus pacemakers and ICDs administer therapy to the heart, in part, based upon the detection of electrical characteristics of the heart such as P-waves, R-waves, atrial rate, ventricular rate, and the like. As one specific example, if the atrial and ventricular rates are both below a minimum acceptable heart rate threshold or if long gaps appear within the IEGM signals wherein no P-waves and R-waves are sensed, the cardiac pacing device thereby concludes that the patient is suffering from bradycardia and administers pacing pulses in an effort to increase the heart rate or to eliminate long gaps without heart beats. As another specific example, if the atrial and ventricular rates are well above a maximum expected heart rate, the cardiac pacing device concludes that the patient is suffering from a tachyarrhythmia and administers appropriate therapy such as, for example, overdrive pacing in an effort to lower the heart rate to within an acceptable range. If the atrial rate is found to be extremely high, but the ventricular rate is relatively normal, the cardiac pacing device concludes that the patient is suffering from atrial flutter or atrial fibrillation and administers a defibrillation pulse to the atria. If the ventricular rate is extremely fast and chaotic, the cardiac pacing device concludes that the patient is suffering from ventricular fibrillation and administers a defibrillation pulse directly to the ventricles. Details regarding techniques for discriminating between atrial and ventricular disrythmias or arrhythmias are provided in U.S. Pat. No. 5,620,471 to Duncan entitled "System and Method for Discriminating Between Atrial and Ventricular Arrhythmias and for Applying Cardiac Therapy Therefor", issued Apr. 15, 1997, which is incorporated by reference herein.

Reliable operation of pacemakers and ICDs therefore necessitates that the device be capable of accurately detecting P-waves, R-waves or other electrical events originating within the heart. Insofar as P-waves are concerned, however, the afore-mentioned R-waves, though initially generated within the ventricles, propagate into the atria and may be detected therein as part of the atrial IEGM signal. It is therefore possible for the device, upon detecting an electrical pulse within the atria, to misidentify a far field R-wave as being a P-wave. As a result, any functions performed by the pacemaker, which require accurate detection of P-waves, may not function as intended. For example, the calculated atrial rate will be higher than the actual atrial rate, perhaps causing the device to erroneously conclude that the atria are subject to a tachyarrhythmia, which does not in fact exist. Alternatively, the overestimated atrial heart rate may cause the device to fail to detect a bradycardia, which does exist. As a result, inappropriate therapy may be administered. For an ICD, an erroneously high determination of the atrial rate may cause the ICD to incorrectly conclude that the heart is subject to atrial fibrillation, resulting in a potentially painful cardioversion pulse administered to the atrium.

Thus, it is necessary to properly distinguish P-waves or other electrical events originating in the atria from far field R-waves or other events originating in the ventricles. Accordingly, most state-of-the-art pacemakers ignore any events detected within the atria during a predetermined period of time subsequent to the detection of an R-wave in the ventricles. This period of time is referred to as the post-ventricular atrial blanking (PVAB) interval or a post-ventricular atrial refractory period (PVARP). Briefly, upon the detection of an R-wave from a sensing electrode positioned within the ventricles, the pacemaker thereafter ignores any events detected from a sensing lead within the atria for a period of time (e.g. 225 ms.) under the assumption that any event detected during that period of time is actually a far field R-wave.

The need to use numerous relative and absolute blanking and refractory periods has various disadvantages. The blanking and refractory periods must be carefully set for the device to function properly. This requires a careful and time-consuming review by the physician of programming parameters used to set the refractory and blanking periods within the implanted device and may necessitate several follow-up sessions between patient and physician before the parameters are set properly. Also, the discrimination algorithm employed by the implanted device is quite complicated and prone to event misidentification.

One example of a problem that can arise when using refractory and blanking periods involves the misidentification of far field R-waves as P-waves. In this regard, the use of a PVAB interval presupposes that the R-wave will be detected in the ventricles before it appears as a far-field R-wave in the atria. This is not always the case. However, circumstances can arise wherein a far field R-wave is detected within the atria before it is detected within the ventricles. This may occur, for example, if an atrial sensing lead is positioned closer to the source of an R-wave than the ventricular sensing leads. Another circumstance wherein an R-wave may be detected within the atria without a preceding R-wave detection in the ventricles occurs if the threshold for R-wave detection in the ventricles is set too high, such that some R-waves are not detected at all within the ventricles. In any event, if the far field R-wave is detected within the atria without an immediately preceding R-wave detection in the ventricles, the aforementioned PVAB interval is ineffective to filter out the far field R-wave from the atrial IEGM. As a result, far field R-waves are misclassified as P-waves resulting in incorrect determination of atrial rate, or other critical parameters, causing potentially erroneous therapy to be administered by the pacemaker.

Another example of a problem that can arise when using refractory and blanking periods involves the miscalculation of high atrial rates when using Combipolar sensing. ("Combipolar" is a trademark of St. Jude Medical.) With Combipolar sensing, a pair of unipolar leads is positioned within the heart, one in the atrium and one in the ventricle. A ventricular channel IEGM signal is generated in the same manner as with unipolar sensing wherein electrical voltage differentials are detected between the tip of the ventricular lead and the body of the device. However, the atrial channel of the IEGM signal is generated by detecting voltage differentials between the electrodes at the tips of the atrial and ventricular leads. A logic system internal to the pacemaker determines whether the signal is an atrial signal or a ventricular signal. More specifically, a signal detected on both the atrial and ventricular channels is regarded as a ventricular signal. A signal detected only on the atrial channel is regarded as a true atrial signal. A signal detected only on the ventricular channel is regarded as being of extracardiac origin. For a more complete description of Combipolar systems, see U.S. Pat. No. 5,522,855 (Hoegnelid), incorporated herein by reference.

However, when using Combipolar sensing, intrinsic ventricular signals are always recorded on the atrial channel. This is not a problem when the intrinsic ventricular signal is also detected on the ventricular channel since the logic of the Combipolar system will regard the signal as being a ventricular signal, but if an intrinsic signal arising in the ventricle is not detected on the ventricular channel but only on the atrial channel, it will be treated as a P-wave. Such may be the case with the T-wave, which typically coincides with the Ventricular Refractory Period (VRP)—a period of time when the ventricular channel is not capable of responding to intrinsic signals. Accordingly, the use of conventional blanking and refractory periods in connection with Combipolar sensing can result in T-waves being misidentified as P-waves, thereby yielding an incorrect atrial rate, particularly at high atrial rates.

Accordingly, it would be desirable to provide an improved technique for detecting electrical events originating within the heart, which does not require use of blanking and refractory periods, and it is to that end that aspects of the present invention are primarily directed.

SUMMARY OF THE INVENTION

In accordance with one aspect of the invention, a technique is provided for detecting electrical events in the heart of the patient without using blanking or refractory periods. Rather, electrical events are detected by comparing signal vectors generated from combinations of electrodes with pre-determined classification zones. The technique is performed by an implantable cardiac stimulation device for implant within a patient wherein the device has multiple electrodes. Electrical signals are sensed by selected combinations of the electrodes and a signal vector is generated that is representative of the electrical signals. Then, the signal vector is compared with a set of predetermined vector classification zones, each representative of a range of signal vectors for different cardiac electrical events, to classify the electrical event. By directly comparing signal vectors with event classification zones, blanking and refractory periods are not required.

In one example, a signal vector is generated by sensing the voltages between various combinations of electrodes, such as sensing an A-tip to V-tip voltage, an A-tip to A-ring voltage, an A-ring to V-ring voltage, an A-ring to V-ring voltage, and a V-ring to coil voltage. The signal vector specifies the amplitudes of the voltage signals derived from those electrode combinations. The signal vector is compared with a set of classification zones, each corresponding to a different event, such as a P-wave, R-wave, T-wave, A-pulse, V-pulse, PAC, or PVC, to determine whether the vector lies within any of the classification zones. The classification zones are each specified by a unique geometrical range, defined by a direction vector, a maximum angle from the vector, a minimum vector length and a maximum vector length. For P-waves, for example, there is a corresponding P-wave zone specifying a P-wave direction vector, a maximum angle from the P-wave direction vector, a minimum P-wave vector length and a maximum P-wave vector length. If the signal vector lies within the geometric range for the P-wave classification zone, the signal vector is thereby identified as being a P-wave. If not, the signal vector is compared with other classification zones. If the signal vector does not lie within the within the geometric range of any for the classification zones, then it is designated as an unclassified event, typically electrical noise.

In another example, rather than comparing individual signal vectors to individual classification zones, a sequence of signal vectors is compared with a sequence of vector classification zones. For example, if a pair of consecutive signal vectors matches a classification zone sequence representing a P-wave followed by a QRS-complex, the pair of events may thereby be identified as being a normal sinus beat. Atrial fibrillation, ventricular fibrillation or other such events may also be detected using these techniques.

In accordance with another aspect of the invention, a technique is provided for determining a set of vector classification zones for a particular patient. The technique may be performed, for example, by a device programmer in communication with an implanted cardiac stimulating device and a surface ECG detector. Signal vectors, generated by the implanted device, are input by the device programmer for various cardiac electrical events in the heart of the patient. ECG signals, generated by a surface ECG detector attached to the patient, are also input by the device programmer. The ECG signals represent the same cardiac electrical events as the signal vectors. The device programmer identifies the electrical events based on ECG signals and then labels the various signal vectors accordingly. Then, for a given event type, the device programmer generates the event classification zone for that event type based on all of the signal vectors that had been correlated with the event type, i.e. all signal vectors labeled as corresponding to the event type based on the ECG analysis.

For example, the device programmer takes all signal vectors identified as being P-waves, based on the ECG, and determines the geometric range for the P-wave classification zone based on the P-wave signal vectors. In this regard, the device programmer determines the P-wave direction vector, the maximum angle relative to the P-wave direction vector, the minimum P-wave vector length and the maximum P-wave vector length. The P-wave direction vector is determined by averaging the directions of all of the individual P-wave vectors. The maximum angle relative to the P-wave direction vector is determined by finding the individual P-wave having the greatest angular deviation from the P-wave direction vector. The maximum P-wave vector length is determined by finding the individual P-wave having the greatest vector length. The minimum P-wave vector length is determined by finding the individual P-wave having the shortest vector length. Preferably a large number of individual cardiac events are detected under different patient conditions before the geometric ranges of the various event types are generated. Also, the resulting geometric ranges are each preferably enlarged by adding safety margins to the minimum vector length, maximum vector length, and maximum angle relative to the direction vector.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENT

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Exemplary systems and methods using signal vectors are described for classifying electrical events, such P-waves, R-waves, etc., sensed within the heart of a patient. The classification method is performed by an implantable cardiac stimulation service subject to programming commands received from an external programmer. Initially, an overview of the implanted device is provided with reference to FIGS. 1 and 2 and an overview of an external programmer used to program the device is then provided with reference to FIG. 3. An overview of the mathematics underlying the vector-based technique is then provided with reference to FIGS. 4–8. An exemplary technique for classifying individual electrical events using the vector-based technique is provided with reference to the flowcharts of FIG. 9. The vector-based technique employs classification zones, which are unique to each patient. An exemplary technique for generating the classification zones is provided with reference to the flowcharts of FIGS. 10–11. Then, an exemplary technique for classifying sequences of electrical events is provided with reference to the flowchart of FIG. 12. In the flow charts, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device or external programmer. Those skilled in the art may readily write such a control program based on the flow charts and other descriptions presented herein.

Implantable Device Overview

Figure 1:
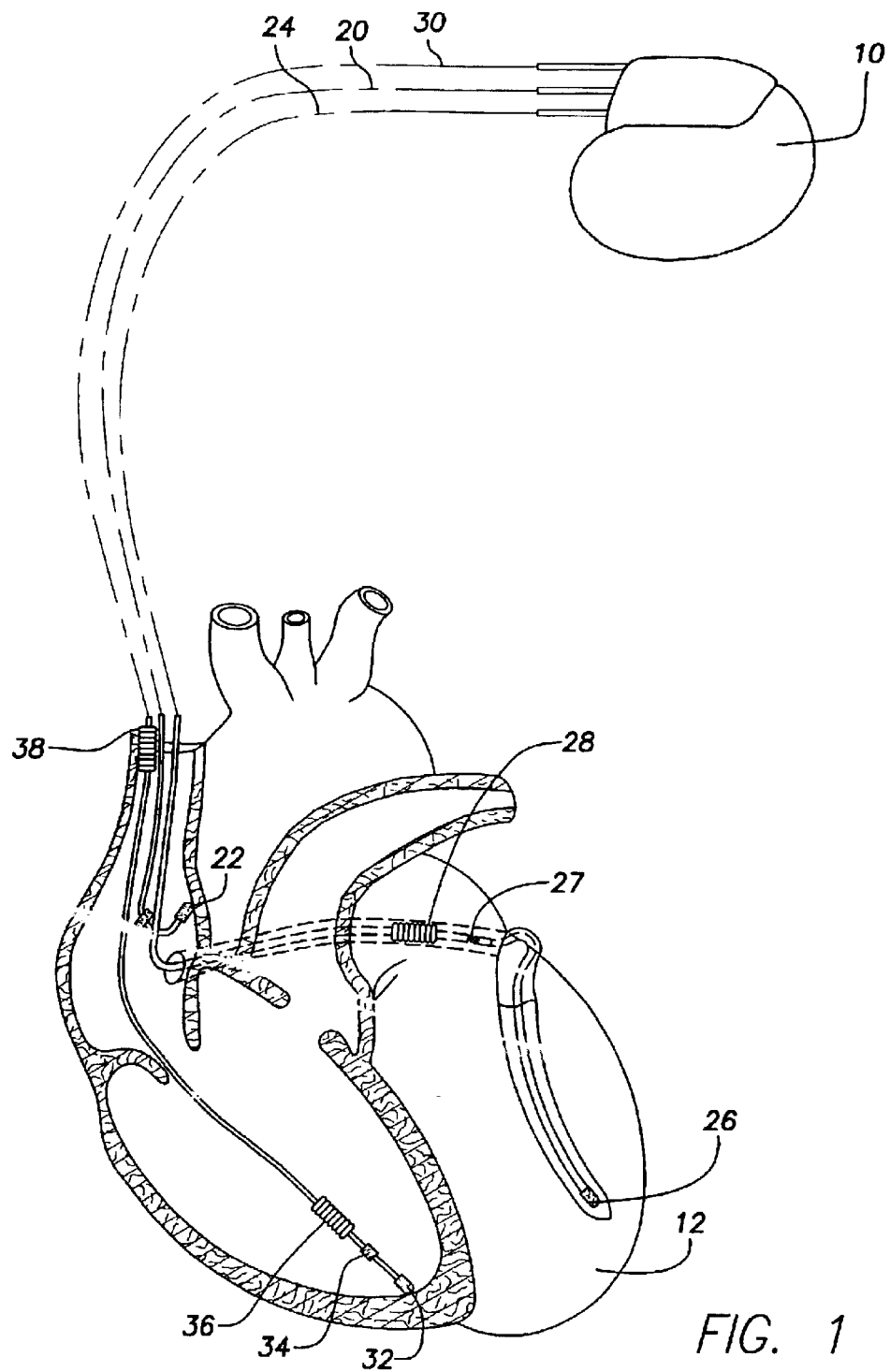
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
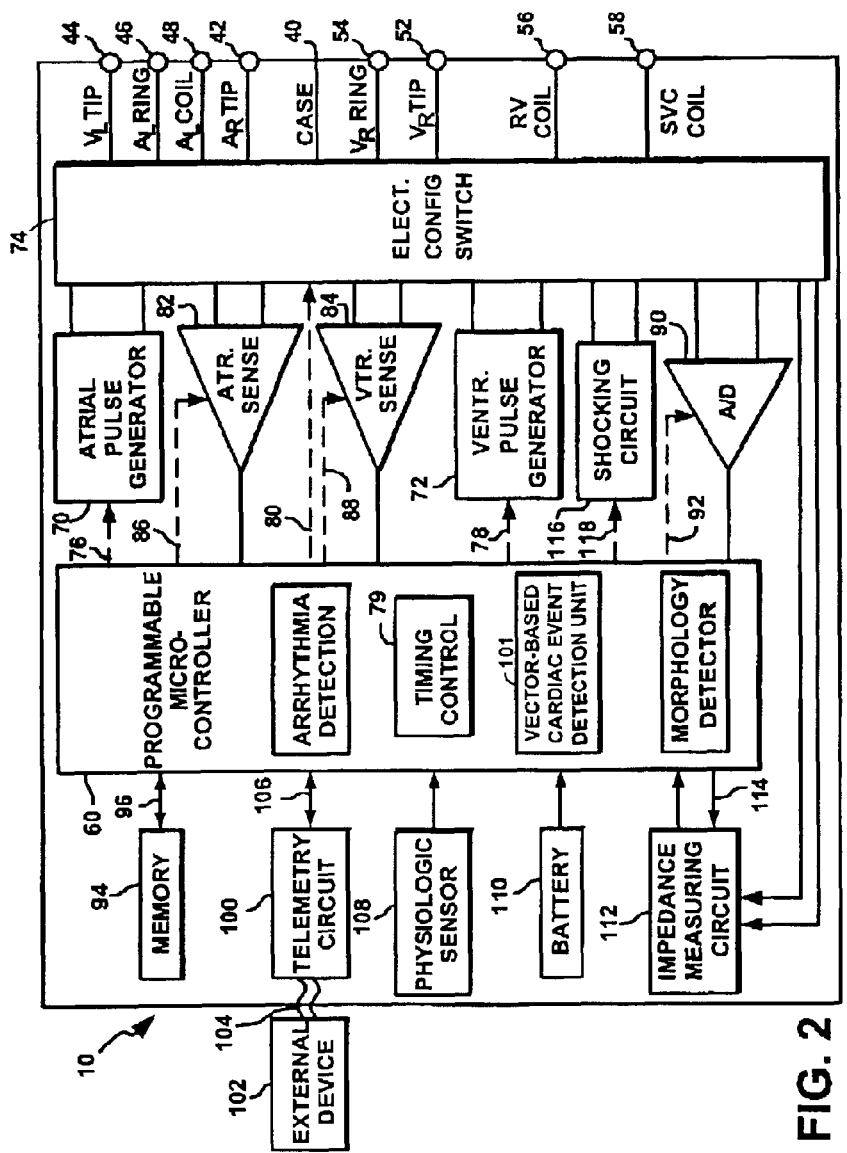
FIG. 2 is a functional block diagram of the multi-chamber implantable stimulation device of FIG. 1 illustrating the basic elements of a stimulation device which can provide cardioversion, defibrillation and pacing stimulation in four chambers of the heart and particularly illustrating a vector-based cardiac event detection unit for classifying electrical events sensed in the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) evoked response windows, alert intervals, marker channel timing, etc., which is well known in the art. The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to sense voltages between any of the electrodes of the right atrial lead 20, coronary sinus lead 24, and the right ventricular lead 30, and the can, through the switch 74 for sensing the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), as is known in the art.

Microcontroller 60 includes a vector-based cardiac event detection unit 101, which operates to detect and classify cardiac electrical events based on signal vectors generated from voltages received from the atrial and ventricular sense amplifiers, in accordance with a technique to be described in detail below primarily with reference to FIGS. 5–9.

For arrhythmia detection, the device 10 utilizes cardiac event detection unit 101 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The operating parameters also include data packets specifying information for use by cardiac event detection unit 101, including 1) events of interest for the particular patient in which the device is implanted; 2) corresponding classification zones for each event of interest; and 3) a set of electrode pair combinations to be activated via switch 74 to sense signal vectors for comparison against the classification zones.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Device Programmer Overview

Figure 3:
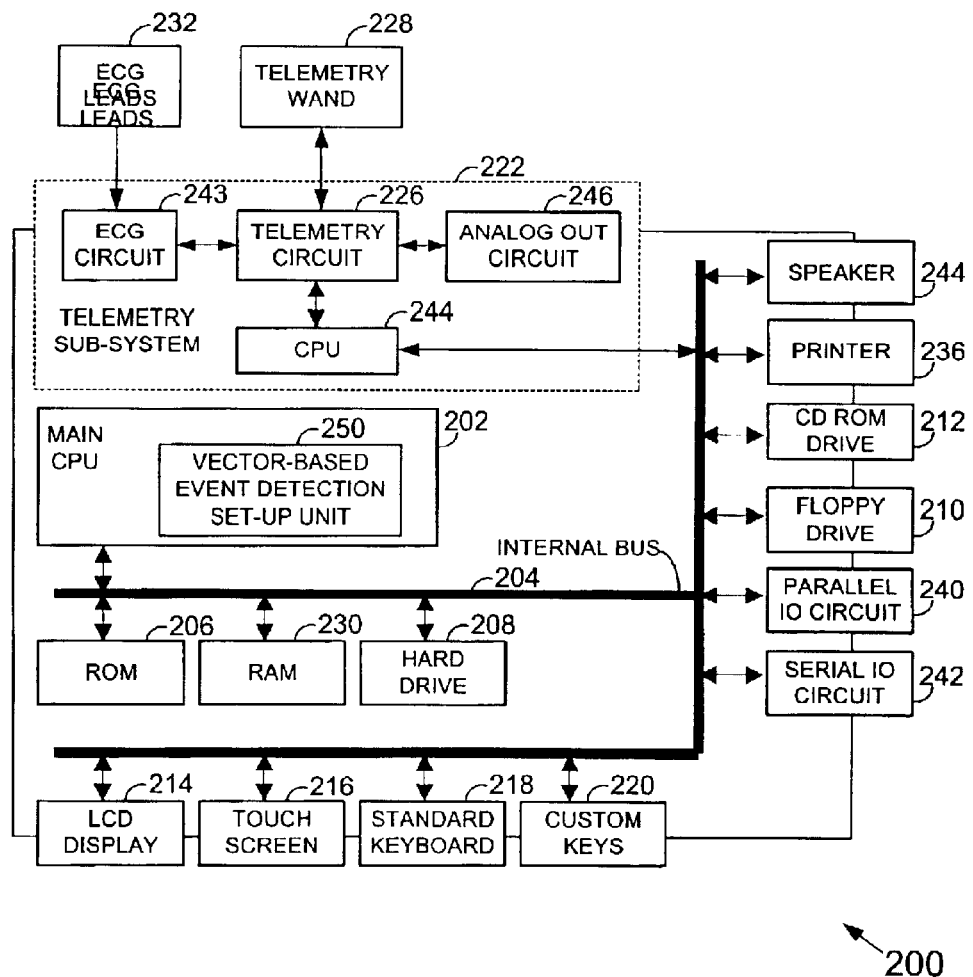
FIG. 3 is a functional block diagram illustrating components of a programmer for use in programming the implantable device of FIG. 1, and in particular illustrating a vector-based event detection set-up unit for use in programming the event detection unit of the implantable device.

FIG. 3 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 200 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus, the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Prior to reprogramming specific parameters, the physician may control the external programmer to display any or all of the data retrieved from the implanted device or from the ECG leads, including displays of ECGs, IEGMs, and statistical patient information. Any or all of the information displayed by programmer may also be printed using a printer 236.

CPU 202 includes a vector-based event detection set-up unit 250 for generating data packets specifying information for use by the vector-based cardiac event detection unit of the implanted device (101 of FIG. 2), including 1) events of interest for the particular patient in which the device is implanted; 2) corresponding classification zones for each event of interest; and 3) a set of electrode pair combinations to be activated within the device to sense signal vectors for comparison against the classification zones. The operation of set-up unit 250 is described in detail below primarily with reference to FIGS. 10 and 11.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and is not intended to provide an exhaustive list of the functions performed by the device.

Event Classification Technique Overview

Briefly, sense amplifiers of the implanted device sense voltages between various combinations of electrodes and the signal vector event detection unit generates a signal vector based on the voltages. The event detection unit compares the signal vector with a set of classification zones specified by an input zone classification kernel. The classification zones each correspond to a different event of interest, such as a P-wave, R-wave, T-wave, A-pulse, V-pulse, PAC, or PVC. The event detection unit determines whether the signal vector lies within any of the classification zones. If the signal vector lies within a classification zone, such as within the P-wave classification zone, the event associated with the signal vector is thereby identified in accordance with the zone in which it lies. If the signal vector does not lie with any of the classification zones, the event is designated as an unclassified event, which may be electrical noise. Once the event has been identified, the microcontroller of the implanted device responds, as needed, to perhaps calculate a new heart rate, modifying pacing therapy, or store diagnostic information.

Figure 4:
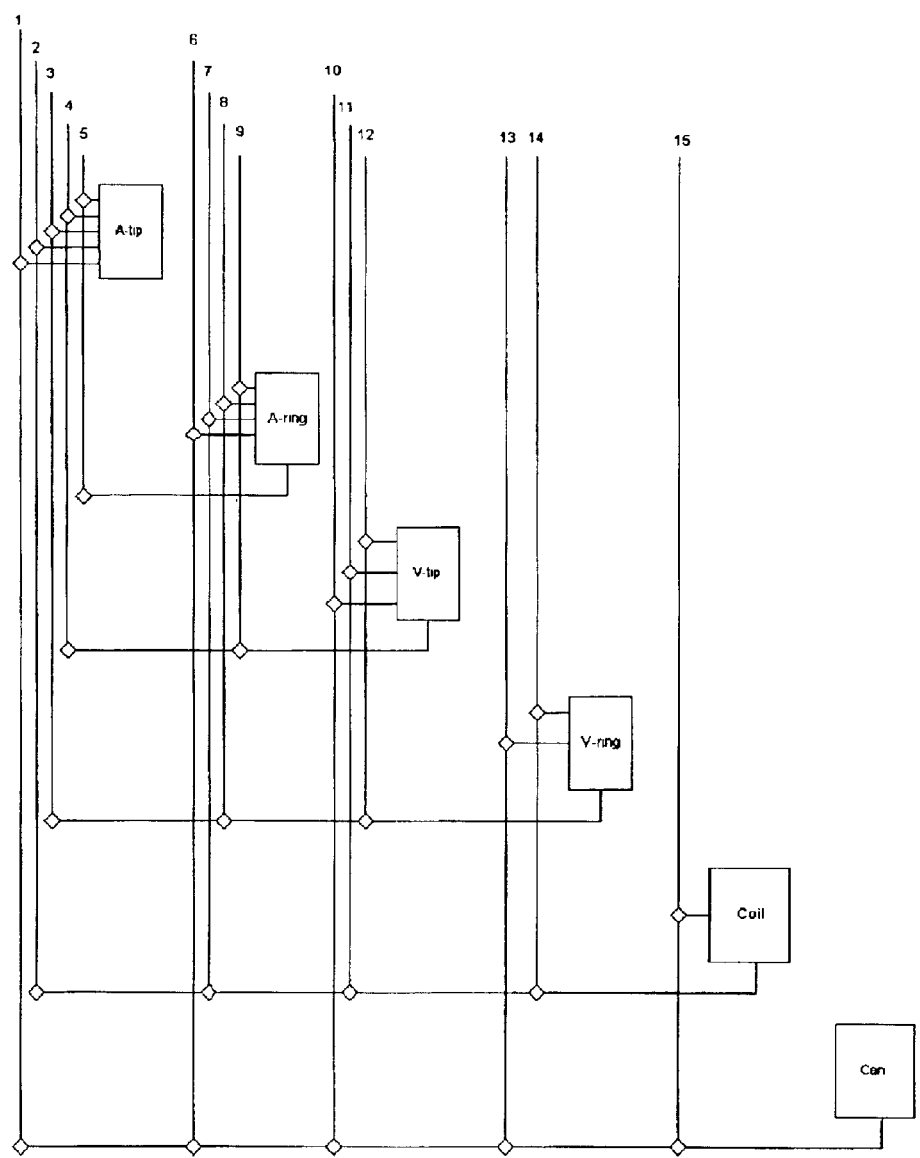
FIG. 4 is a logic circuit diagram illustrating an exemplary portion of the sensing circuitry of the device of FIG. 2, which provide signals to the vector-based event detection unit.

More specifically, since voltage is measured as the difference in potential between any two points, a voltage can be measured between any combination of the electrodes of FIG. 1 and between those electrodes and the device can. FIG. 4 illustrates a specific example of switching circuit 74 (of FIG. 2) wherein the device senses signals only between the A-tip, A-ring, left V-tip, left V-ring, atrial coil and device can, thus generating fifteen different voltage signals, numbered 1–15. The additional electrodes available in the bi-ventricular device of FIG. 1 permit more combinations of electrode pairs. The fifteen signals depicted in FIG. 4 are shown for illustrative purposes only.

Consider signals 1, 4, 5, 8, 9, 10, 12, 14, and 15 of FIG. 4. Values $a_1$ through $a_9$ represent the voltage amplitude values of these nine signals, as shown in TABLE I:

TABLE I

| AMPLITUDE VALUE | SIGNAL | ELECTRODE COMBINATION |
|---|---|---|
| $a_1$ | 1 | A-TIP TO CAN |
| $a_2$ | 4 | A-TIP TO V-TIP |
| $a_3$ | 5 | A-TIP TO A-RING |
| $a_4$ | 8 | A-RING TO V-RING |
| $a_5$ | 9 | A-RING TO V-TIP |
| $a_6$ | 10 | V-TIP TO CAN |
| $a_7$ | 12 | V-TIP TO V-RING |
| $a_8$ | 14 | V-RING TO COIL |
| $a_9$ | 15 | COIL TO CAN |

Figure 5:
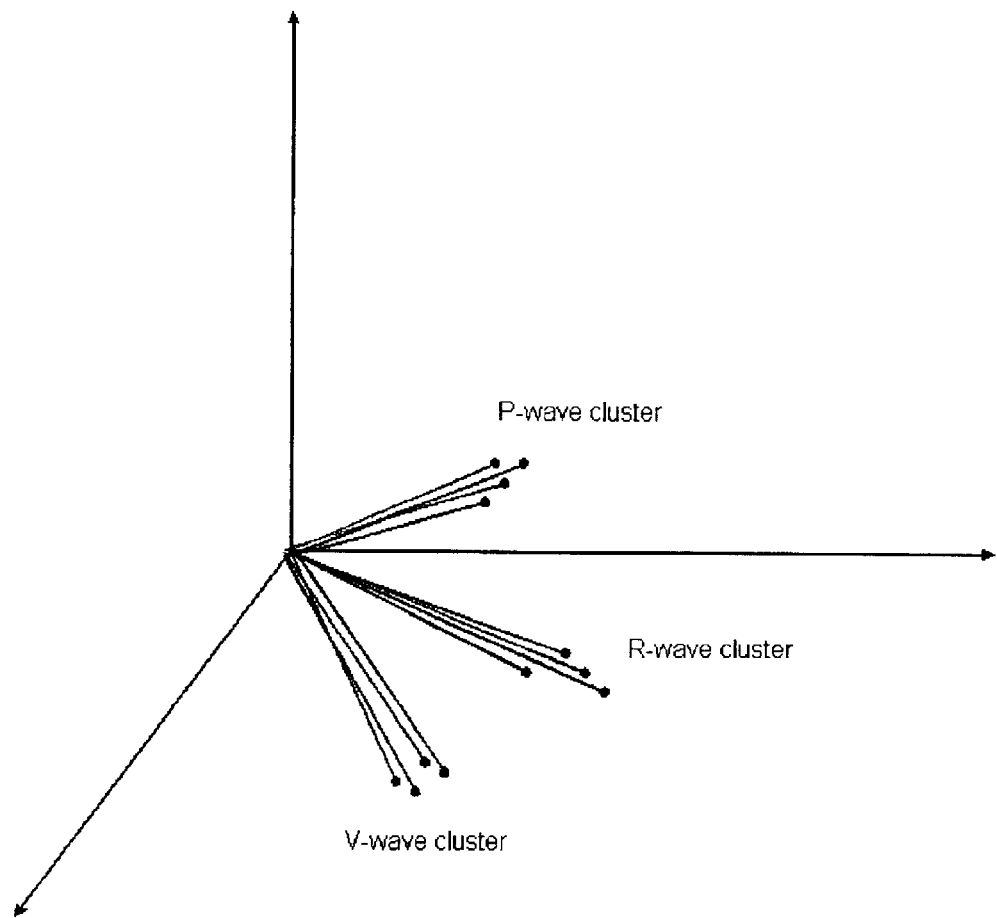
FIG. 5 is a graphic representation of a first exemplary set of signal vector clusters processed by the vector-based event detection unit of FIG. 2.

Taken together, the signals are represented as a vector, $[a_1, \ldots, a_9]$, abbreviated as A. The specific values of $a_1$ through $a_9$ typically vary significantly for different types of cardiac events, such as P-waves or R-waves, as each signal, or vector element, senses the event from a different location. In a P-wave, for example, the $a_3$ component is typically the strongest, with the $a_1$ component the next strongest, the $a_2$, $a_4$, and $a_5$ components at various strengths less than $a_1$, and the remaining components having various strengths even less than those of $a_2$, $a_4$, and $a_5$. In an R-wave, $a_7$ and $a_8$ typically are the strongest, $a_6$ and $a_9$ are next strongest, $a_2$, $a_4$, and $a_5$ are weaker, and $a_1$ and $a_3$ are the weakest. Thus, each different type of cardiac event, i.e., event type, evokes signal vectors characteristic of that event type. It has been found that signal vectors evoked by a given event type cluster within a geometric region characteristic of that event type, as illustrated by the simplified three-dimensional representation in FIG. 5, which shows only the $a_1$, $a_2$, and $a_3$ signal components. Such regions are referred to herein as classification zones. Each event type, e.g., P-wave, A-wave, R-wave, V-wave, etc., has its own, unique classification zone. Note that the three-dimensional representation of FIG. 5 is merely illustrative of the concepts involved. No multi-dimensional graphic representations need be generated to actually implement the invention.

For any given implantable medical device, e.g., dual-chamber defibrillator, single chamber pacer, etc., certain event types are of interest to that device. For each of these event types, a corresponding classification zone is generated (by techniques described below) that correlates to that event type. The resulting set of classification zones correlating to the event types of interest for a particular device is referred to herein as the kernel for that device. In a dual chamber pacemaker, for example, if the event types of interest are P-waves, A-waves, R-waves, and V-waves, then the kernel consists of the classification zones $Z_p$, $Z_a$, $Z_r$, and $Z_v$ that correlate to P-waves, A-waves, R-waves, and V-waves, respectively. The classification zones are patient specific and are therefore preferably customized, or modeled, individually for each patient. An exemplary method for modeling the kernel for a specific device and patient is described below.

Once the kernel for a particular device and patient has been modeled, the kernel serves as a key for classifying individual events, or event instances, sensed in that patient. Each event instance produces a signal vector for comparing with the classification zones which, as noted, correlate to specific event types. The event instance is thereby classified. Using the above example, if event instance E produces signal vector A, then A is compared to each of the classification zones $\{Z_p, Z_a, Z_r, Z_v\}$ in the kernel. If A matches $Z_a$, then E is classified as an A-wave.

As noted, signal vectors produced by event instances of a given event type cluster within a region, or zone, that is characteristic of that event type. The cluster exhibited by an event type is reduced to a mathematical model that approximates and contains the cluster and thereby defines the classification zone correlating to the event type. Repeating this process for each event type of interest yields a model of each of the classification zones in the kernel. Any one of several possible mathematical models may be used for this purpose. An exemplary model is described below. To maximize flexibility in setting safety margins and to minimize the possibility of inconclusive classifications, it is desirable to maximize the separation between the clusters characteristic of different event types.

Consider again the example of TABLE I above wherein values $a_1$ through $a_9$ represent signal sources 1, 4, 5, 8, 9, 10, 12, 14, and 15, respectively. This produces a nine-dimensional vector space with individual vectors comprised of values from signal sources 1, 4, 5, 8, 9, 10, 12, 14, and 15. However, this combination of signal sources is only one example; many different combinations of signal sources are possible. As another example, values $a_1$ through $a_7$ could represent signal sources 1, 3, 5, 6, 11, 13, and 14, respectively, giving rise to a seven-dimensional vector space. The specific combination, or subset, of signal sources being used for a given device is referred to herein as the signal space.

Figure 6:
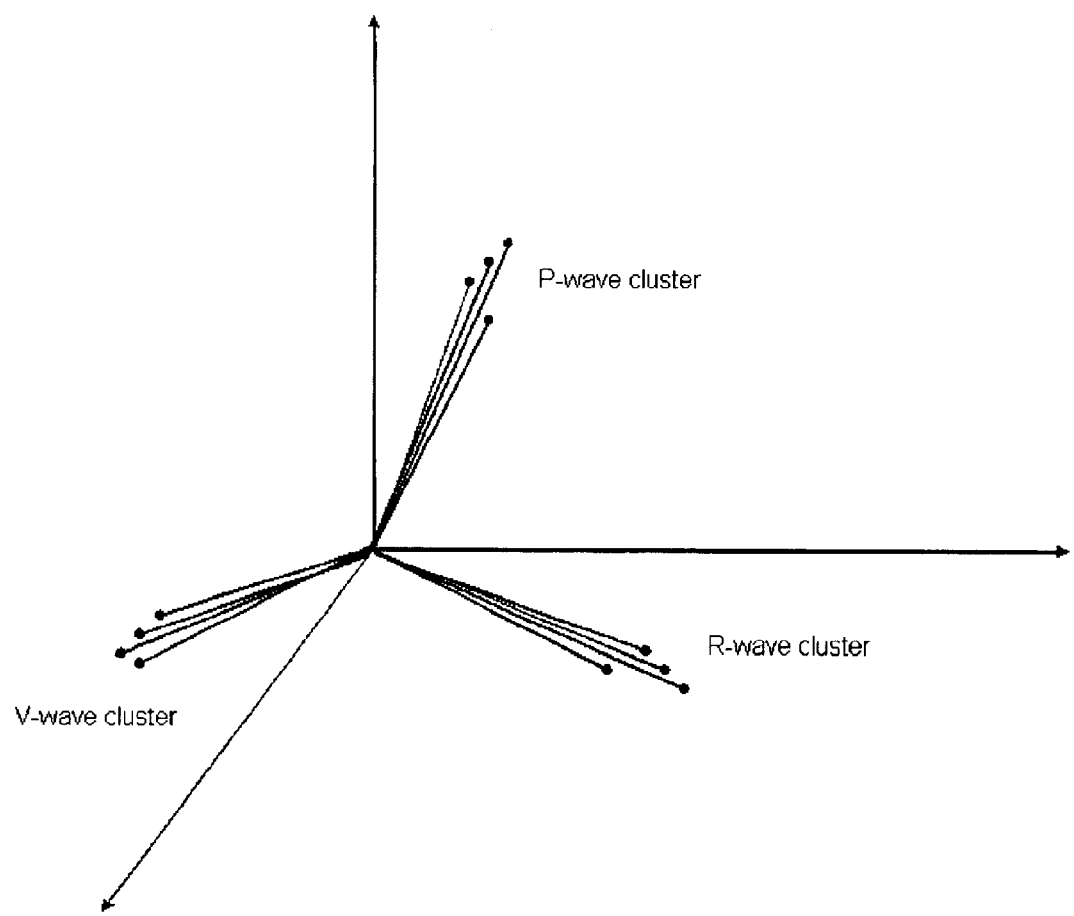
FIG. 6 is a graphic representation of a second exemplary set of signal vector clusters also processed by the vector-based event detection unit of FIG. 2.

Separation is visualized three dimensionally as spatial separation, as can be seen from comparing the smaller separation of FIG. 5 with the larger separation in FIG. 6. More specially, FIG. 5 illustrates the relatively small separation between intrinsic R-wave and paced V-wave clusters expected within the signal space comprised of signals 4 (A-tip to V-tip), 5 (A-tip to A-ring), and 6 (A-ring to Can). FIG. 6 illustrates the relatively larger separation between R-wave and V-wave clusters expected within the signal space comprised of signals 7 (A-ring to Coil), 8 (A-ring to V-ring), and 10 (V-tip to Can).

The amount of separation between clusters is, to some degree, a function of signal space. Selecting a signal space that maximizes the separation between clusters is a part of the modeling process described below. Preferably, the implanted device is configured to provide access to all the signal sources possible for the device and the software embedded in the device is configured to enable the clinician to customize the subset of signal sources, i.e., the signal space, to be used for a given patient and device.

With kernel modeling it is preferred that event instances, and their observed signal vectors, be grouped according to event type so that the resulting clusters can be used to define classification zones. This requires that each event instance be classified according to its event type. Classification zones are not used in the modeling process because they are not defined until after the modeling process is complete. Therefore, an external frame of reference for classifying event instances is used during the modeling process. The surface ECG provides such a frame of reference. By synchronizing to the surface ECG, each event instance can be classified according to the surface ECG indication at the time that event instance occurred.

Figure 7:
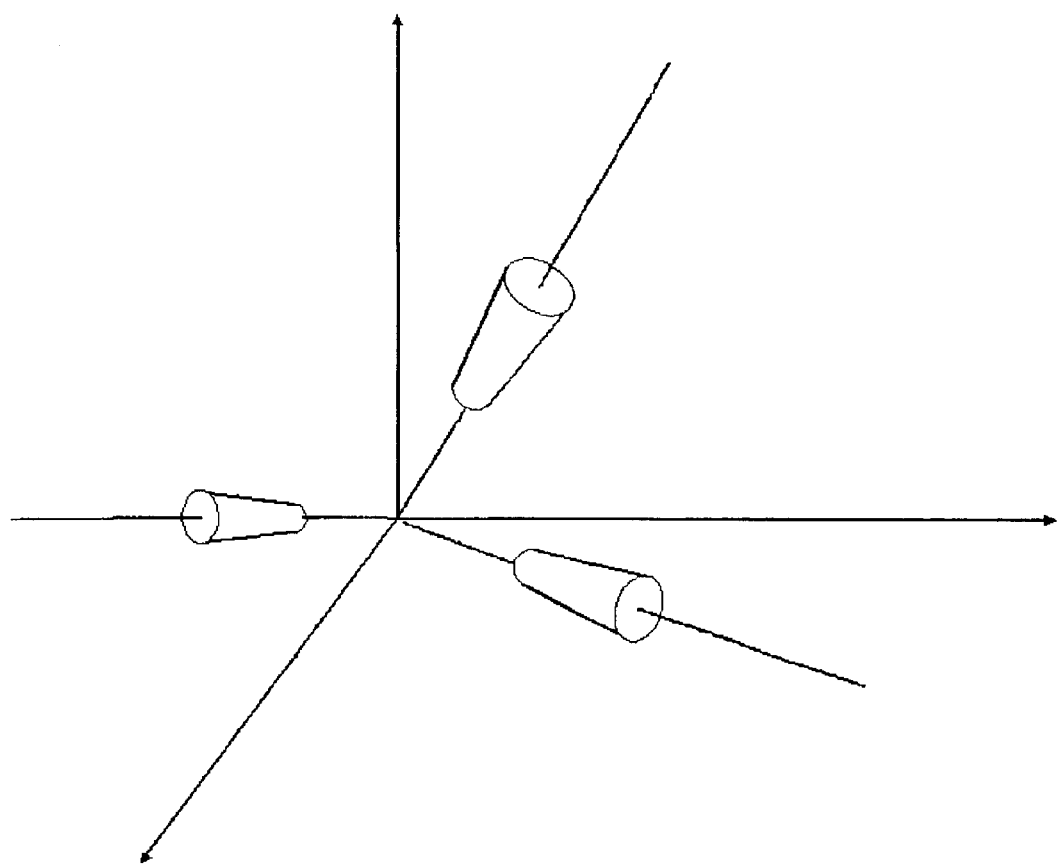
FIG. 7 is a graphic representation of an exemplary set of classification zones used by the vector-based event detection unit of FIG. 2 to identify signal vectors such as those of FIGS. 5 and 6.

In the preferred implementation, the classification zone is represented as an aggregate of two components: a direction vector and a geometric range. The geometric range component, in turn, is an aggregate consisting of a maximum angle relative to the direction vector and a minimum and maximum length. This representation of classification zones is visualized in three-dimensional space as truncated conical sections, as depicted in FIG. 7.

To model the classification zone for an event type, the constituent components of the classification zone—direction vector and geometric range—are generated from a cluster of signal vectors measured for that event type. The direction vector is the average of the individual signal vectors. If $(a_{1,1}, a_{1,2}, \ldots, a_{1,9})$, $(a_{2,1}, a_{2,2}, \ldots, a_{2,9})$, $\ldots$, $(a_{n,1}, a_{n,2}, \ldots, a_{n,9})$ represent n measurements taken from nine electrode pairs of TABLE I, then the average, $\alpha$, or $(\alpha_1, \alpha_2, \ldots, \alpha_9)$, is given by $$\alpha = (\alpha_1, \alpha_2, \ldots, \alpha_9)$$
$$= [(a_{1,1} + a_{2,1} + \ldots + a_{n,1})/n,$$
$$(a_{1,2} + a_{2,2} + \ldots + a_{n,2})/n, \ldots, (a_{1,9} + a_{2,9} + \ldots + a_{n,9})/n].$$

For a generalized system employing m electrode pairs, with $(a_{1,1}, a_{1,2}, \ldots, a_{1,m})$, $(a_{2,1}, a_{2,2}, \ldots, a_{2,m})$, $\ldots$, $(a_{n,1}, a_{n,2}, \ldots, a_{n,m})$ representing n measurements, then the average, $\alpha$, or $(\alpha_1, \alpha_2, \ldots, \alpha_m)$, is given by $$\alpha = (\alpha_1, \alpha_2, \ldots, \alpha_m)$$
$$= [(a_{1,1} + a_{2,1} + \ldots + a_{n,1})/n,$$
$$(a_{1,2} + a_{2,2} + \ldots + a_{n,2})/n, \ldots, (a_{1,m} + a_{2,m} + \ldots + a_{n,m})/n].$$

The geometric range component of the classification zone consists of a maximum angle relative to the direction vector, a minimum length, and a maximum length. The minimum and maximum lengths are determined by computing the norm, or length, of each of the individual signal vectors. The smallest norm, less some safety margin, becomes the minimum length and the largest norm, plus some safety margin, becomes the maximum length. Similarly, the maximum angle is determined by computing the angle between each signal vector, $a_i$, and the average vector, $\dot\alpha$. The largest of these values, plus some safety margin, becomes the maximum angle relative to the direction vector. The angle between $a_i$ and $\dot\alpha$ is given by the following formula:

$$\Theta = \cos^{-1}[(a_i \cdot \dot\alpha)/(\|a_i\| \|\dot\alpha\|)]$$

where $a_i \cdot \dot\alpha$ is the dot-product, or inner product, of $a_i$ and $\dot\alpha$, given by $$(a_{i,1})(\tilde{a}_1) + (a_{i,2})(\tilde{a}_2) + \ldots + (a_{i,m})(\tilde{a}_m)$$

Figure 8:
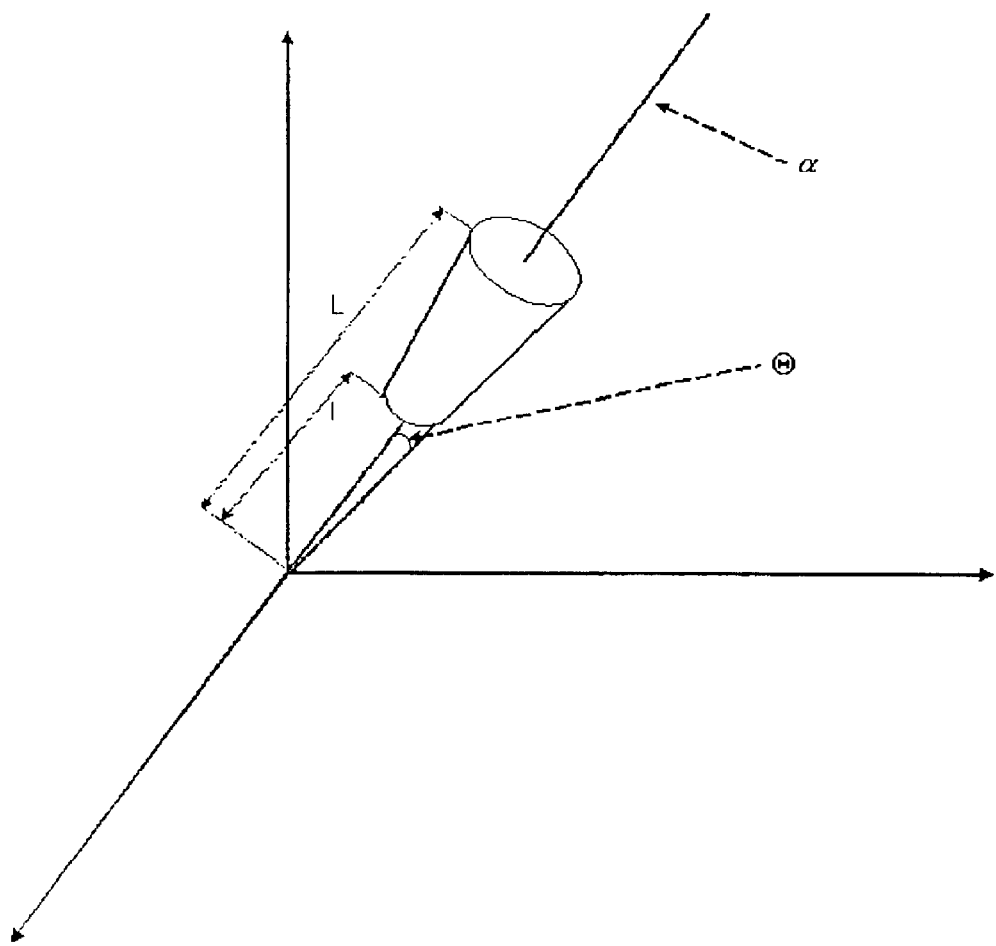
FIG. 8 is a graphic representation of single exemplary classification zone used by the vector-based event detection unit of FIG. 2, particularly illustrating geometric parameters associated therewith.

$\|a_i\|$ is the norm of $a_i$, given by $$(a_{i1}^2 + a_{i2}^2 + \ldots + a_{im}^2)^{1/2}$$

and $\|\dot\alpha\|$ is the norm of $\dot\alpha$.
This is represented using the following notation $$Z_i = \{\dot\alpha_i, \Theta_i, I_i, L_i\}$$

where $Z_i$ is a classification zone and $\dot\alpha_i$, $\Theta_i$, $I_i$, and $L_i$ represent the direction vector, maximum angle, minimum length, and maximum length, respectively. FIG. 8 illustrates these geometric parameters in three-dimensional space.

Given this model, an event instance is then classified by matching its resulting signal vector to a classification zone. This is accomplished by comparing the signal vector to each classification zone in the kernel. A classification zone, $Z_i = \{\dot\alpha_i, \Theta_i, I_i, L_i\}$, is said to match, or contain, signal vector A if $$I_i <= \|A\| <= L_i \quad (1)$$

and $$(A \cdot \dot\alpha)/(\|A\| \|\dot\alpha\|) <= \cos \Theta_i \quad (2)$$

When a signal vector is compared to a classification zone, all components of the signal vector are used in the comparison. Therefore, none of those components need be ignored or suppressed by employing refractory or blanking periods. Stated another way, once a signal space has been selected for a kernel, all constituent signals of that signal space are used in the classification process without the need for refractory or blanking periods.

Individual Event Classification Method

Specific steps taken by the implanted device to implement the technique outlined above will now be described with reference to FIG. 9. Initially, at step 300, the vector-based cardiac event detection unit of the implanted device inputs a zone classification packet from the external programmer that specifies: 1) events of interest for the particular patient in which the device is implanted; 2) corresponding classification zones for each event of interest; and 3) a set of electrode pair combinations to be used by the device to sense signal vectors for comparison against the classification zones. The zone classification packet is a package of data that encodes the foregoing information in numerical form, in accordance with conventional computer techniques. Preferably, the zone classification packet is configured to represent the classification zones using the kernel-based technique described above, but may alternatively be configured to specify classification zones using other techniques as well. TABLE II illustrates the data provided in an exemplary zone classification packet.

TABLE II

| EVENTS OF INTEREST | CLASSIFICATION ZONE |
|---|---|
| P-WAVE | P-WAVE ZONE: |
|  | P-WAVE DIRECTION VECTOR |
|  | P-WAVE MINIMUM LENGTH |
|  | P-WAVE MAXIMUM LENGTH |
|  | P-WAVE MAXIMUM ANGLE |
| R-WAVE | R-WAVE ZONE: |
|  | R-WAVE DIRECTION VECTOR |
|  | R-WAVE MINIMUM LENGTH |
|  | R-WAVE MAXIMUM LENGTH |
|  | R-WAVE MAXIMUM ANGLE |
| T-WAVE | T-WAVE ZONE: |
|  | T-WAVE DIRECTION VECTOR |
|  | T-WAVE MINIMUM LENGTH |
|  | T-WAVE MAXIMUM LENGTH |
|  | T-WAVE MAXIMUM ANGLE |
| A-PULSE | A-PULSE ZONE: |
|  | A-PULSE DIRECTION VECTOR |
|  | A-PULSE MINIMUM LENGTH |
|  | A-PULSE MAXIMUM LENGTH |
|  | A-PULSE MAXIMUM ANGLE |
| V-PULSE | V-PULSE ZONE: |
|  | V-PULSE DIRECTION VECTOR |
|  | V-PULSE MINIMUM LENGTH |
|  | V-PULSE MAXIMUM LENGTH |
|  | V-PULSE MAXIMUM ANGLE |

| ELECTRODE PAIRS | |
|---|---|
| A-TIP TO CAN | V-TIP TO CAN |
| A-TIP TO V-TIP | V-TIP TO V-RING |
| A-TIP TO A-RING | V-RING TO COIL |
| A-RING TO V-RING | COIL TO CAN |
| A-RING TO V-TIP | |

The events of interest specified in the packet typically include, as shown in the table, P-waves, R-waves, T-waves, A-pulses, and V-pulses, and may additionally include other electrical cardiac events, such as PAC's, PVCs, and the like. In general, each and every type of event that the implanted device must detect in order to administer therapy is specified. Additionally, events of purely diagnostic interest may be specified. Rather than specify the events of interest in the packet, the list of events may be preprogrammed into the device at device manufacture. In such case, the kernel need only specify the classification zones associated with the pre-programmed events of interest.

In the example, of TABLE II, each zone is a representative of a truncated multi-dimensional cone defined in terms of direction, vector, minimum length, maximum length, and maximum angle, in accordance with the mathematical model detailed above. However, alternative techniques may be employed for specifying the classification zones. Indeed, different shaped zones may be employed for the various event types. For example, the P-wave zone may be represented as a multidimensional sphere specified by a center point and a radius, whereas the R-wave zone may be represented as a multidimensional ellipsoid specified by a center point and an appropriate number of semi-axes. The use of truncated cones is preferred as it is relatively easy to implement but, in general, any appropriate geometric zone shape or shapes can be used so long as they permit cardiac events to be uniquely identified. Multiple zones per event can also be specified with, for example, a first set of zones used as a primary set for classifying events and a second set employed for events deemed unclassifiable using the first set of zones. Or different zones can be used based on the current mode of operation of the device or condition of the patient. For example, one set of zones might be used while the device is in a tracking mode and another in a non-tracking mode or one set might be used while the patient is at rest and another while active. Similarly, whereas the example of TABLE II provides a single set of electrode pairs for use in detecting all events, multiple sets of electrode pairs can alternatively be specified. Again, a first set might be used as a primary set for classifying events and a second set employed for events deemed unclassifiable using the first set of electrode pairs. As can be appreciated, a wide range of alternative embodiments may be implemented consistent with the general principles of the invention and no attempt is made herein to itemize all possible variations.

At step 302, the event detection unit controls the implanted device to activate sense amplifiers associated with the electrode pairs specified in the zone classification packet and, at step 304, begins receiving voltage signals from the pairs of electrodes. The voltages change continuously with time. Whenever the voltages exceed some predetermined threshold, indicative of a possible cardiac electrical event, the voltages are sampled and a signal vector is generated at step 306. In one implementation, voltages from all of the selected electrode pairs are converted to positive voltages then combined, and a signal vector is generated only if the combined voltage exceeds a threshold voltage. In another implementation, each separate voltage is compared against a threshold voltage and a signal vector is generated whenever any of the voltages exceeds its respective threshold voltage. Once the threshold has been exceeded, indicative of a possible cardiac electrical event, the analog voltages are converted to digital values using analog-to-digital (A-to-D) converters, and the digital values are then stored internally within a data array having a separate numerical value for each electrode pair. Thus the signal vector is a numerical representation of a possible cardiac electrical event occurring in the heart, which may be, for example, a P-wave or R-wave. At step 308, the signal vector is compared with the set of classification zones in an attempt to classify the event.

In still other implementations, rather than comparing electrode pair voltages against threshold voltages, the voltages are first converted to digital values to yield a signal vector. The signal vector is then compared against a numerical threshold and, if it does not exceed the threshold, the signal vector is discarded. Only signal vectors that exceed the numerical threshold are compared, at step 308, with the set of classification zones in an attempt to classify the event. In one specific implementation, the numerical threshold is defined as the smallest of the minimum lengths of each of the classification zones. If the length of the signal vector is smaller than the numerical threshold value, it will necessarily be smaller than the minimum length for any classification zone and will therefore not yield a classifiable event. Alternative threshold comparison techniques may be employed as well. The specific technique that is most effective may be determined via routine experimentation.

In any case, as noted, the signal vector is compared at step 308 with the set of classification zones in an attempt to classify the event. The comparison at step 308 is performed by sequentially comparing each classification zone with the signal vector until a classification zone is found that matches the vector. If using the mathematical model described above, classification zone, $Z_i = \{\dot{\alpha}_i, \Theta_i, I_i, L_i\}$, is said to match, or contain, signal vector A if $I_i <= \|A\| <= L_i$ and $(A \cdot \dot\alpha)/(\|A\| \|\dot\alpha\|) <= \cos \Theta_i$. Each of the forgoing mathematical values is internally represented using data variables or arrays and the mathematical comparisons are performed in accordance with otherwise conventional computing techniques.

If the signal vector matches one of the classification zones, the electrical event in the heart represented by the signal vector is classified based on the zone at step 310. Thus, if the signal vector matched the P-wave zone, the event is classified as a P-wave; if the signal vector matched the R-wave zone, the event is classified as a R-wave; and so on. The zones are mutually exclusive so that a signal vector will match, at most, one and only one zone. If the signal vector does not match any of the classification zones, the electrical event is deemed to be unclassified, at step 312, and diagnostic data is stored identifying the unclassified event. The event may represent noise. During a follow-up session with the physician, the diagnostic data may be reviewed and, if the number of unclassified events exceeds some threshold, the physician may be prompted to modify the electrode combination or to specify additional events of interest. In any case, step 314 is then performed wherein the event detection unit forwards the results of the classification process to the microcontroller for use in controlling operations of the implanted device to, for example, administer cardiac pacing or defibrillation therapy to the patient or to store diagnostic information. Processing then immediately returns to step 304 to sense and classify the next event.

Steps 304 to 314 are performed continuously in a loop at all times while the implanted device is operating within the patient to continuously detect cardiac events, if any, and deliver appropriate therapy. Note that the microcontroller does not typically base therapy delivery decisions on detection of a single event but on information gained from a collection of events. For example, the detection of several R-waves within a given period of time permits the microcontroller to determine the heart rate of the patient, which may then trigger delivery of cardioversion shocks if the heart rate exceeds some threshold. Hence, it may be necessary to detect a number of events using steps 304–314 before therapy is actually delivered. In general, the microcontroller processes the event classification information provided by the vector-based event detection using otherwise conventional techniques. No attempt is made herein to describe such processing in detail.

Exemplary Classification Zone Generation Method

Specific steps performed to set-up the classification zones will now be described with reference to the FIGS. 10 and 11. The set-up method is preferably performed immediately following implant of the device as the implanted device is not able to detect cardiac signals until set-up has been performed. Alternatively, default classification zones are pre-programmed into the device to permit the device to begin operating immediately, and the set-up method is performed later to "fine tune" the classification zones for the particular patient. In any case, the classification zones are generated by the vector-based event detection set-up unit of the external programmer using signals received simultaneously from the implanted device and from a surface ECG unit strapped to the chest of the patient. Steps performed by the surface ECG unit, the external programmer and the implanted device are shown on the left, middle and right sides of FIG. 10, respectively. At step 400, the external programmer inputs a list of cardiac events of interest for the patient from the physician or other clinician operating the external programmer. The selection of the events depends, in part, on the particular condition of the patient such as any chronic dysrhythmias. The list of events typically includes, at least, P-waves, R-waves, T-waves, A-pulses, and V-pulses but may additionally include other events, such as PAC's, PVCs, and the like, deemed important by the physician. At minimum, every event the implanted device must detect in order to be able to make therapy delivery decisions must be specified. Additionally, events that are merely of diagnostic interest may also be specified. Preferably, the external programmer is configured to generate a default list of events based on the capabilities of the implanted device and based on whatever other programming commands have been specified by the physician (such as whether the physician has enable overdrive pacing or the like). The default list is presented to the physician for review and the physician can then expand the list if so desired. Alternatively, the implanted device is preprogrammed with a fixed list of detectable events, which the external programmer retrieves from the implanted device via telemetric interrogation. If so, no user input from the physician is required, though the programmer is preferably configured to present the list to the physician, if requested.

Based on the list of events to be detected by the implanted device, the programmer then retrieves, at step 402, a pre-stored list of the preferred or optimal combinations of electrode pairs needed to detect the events. For example, if the list of events includes only P-waves, R-waves, T-waves, A-pulses, and V-pulses, the optimal combination of electrodes may specify the following combination of electrode pairs as the optimal combination: A-tip to can, A-tip to V-tip, A-tip to A-ring, A-ring to V-ring, A-ring to V-tip, V-tip to can, V-tip to V-ring, V-ring to coil, and coil to can. If the list of events additionally includes PAC's, PVCs, the optimal combination of electrodes may specify additional electrode pairs. The list of optimal electrode pairs also depends on the particular capabilities of the implanted device and the arrangement of leads. Thus, for a particular combination of events to be detected, one set of optimal electrode pairs may be specified for use with bipolar pacing leads whereas another set is specified for use with monopolar leads. The list of optimal electrode pairs may also depend upon the characteristics of the patient such as gender, age, weight, generally activity level, chronic dysrhythmias etc.

The optimal combinations of electrode pairs may be determined in advance based on a statistical analysis of the distribution of signal vectors for each of type of cardiac events taken from a population of patients. More specifically, for each detectable event, signal vectors from a population of patients are detected and analyzed to determine the specific combination of electrodes that provides the optimal clustering of signal vectors to permit the most reliable event detection. The optimal cluster is typically one wherein events of the same type (such as P-waves) always yield a closely-adjacent clustering of signal vectors regardless of heart rate, gender, age, etc. but wherein events of differing types (such as P-waves vs. R-waves) always yield a wide cluster separation, also regardless of heart rate, gender, age, etc. In this manner, electrode combinations are identified that can be reliably used to discriminate among the different types of events regardless of heart rate, gender, age, etc. The optimal electrode combinations are then pre-programmed into the external programmer for use with the method of FIG. 10. If two or more electrode combinations are equally effective in discriminating among the events (i.e. the cluster separations are generally the same), the combination requiring the fewest number of electrode pairs is preferred, so as to reduce the processing burden within the implanted device. If different electrode combinations are to be employed depending upon the characteristics of the patient, studies are performed on populations of patients having differing characteristics, such as different age groups, genders etc., to permit the determination of a set of optimal electrode combinations. In this manner, different optimal electrode combinations may be generated for use with different age groups, genders, etc. As can be appreciated, a wide range of techniques are available for determining and specifying optimal electrode combinations consistent with the principles of the invention and no attempt is made herein to list all possible techniques. In general, the studies employed to determine the optimal electrode combinations may be performed in accordance with routine experimental techniques using routine statistical analysis techniques and, accordingly, will not be described in further detail herein.

Beginning, at step 404, the external programmer activates the surface ECG unit to begin collecting surface ECG data (at step 406), which is transmitted to the external programmer (at step 408) for storage therein. Also at step 404, the external programmer controls the implanted device to begin generating signal vectors (at step 410), which are also transmitted to the external programmer (at step 412) for storage therein. Thus, surface ECGs and signal vectors are collected simultaneously from the patient and hence represent the same electrical events within the heart of the patient. Data is collected over a period of time, typically at least a half hour, to thereby obtain a statistically significant amount of data from which classification zones can be generated. Within a half hour, about 1800 samples can be collected (30 minutes times approximately 60 beats per minute). Less frequent events, such as PVCs, do not occur with nearly that frequency but can be induced in the patient so as to permit collection of the necessary event samples. Preferably, the patient is asked to exercise during a portion of this time and to rest during a portion of this time to obtain data for a variety of exercise states, although this may not be feasible if the device has just been implanted.

Once a sufficient amount of data has been obtained, the set-up unit of the external programmer, at step 414, identifies the various cardiac events appearing in the ECG using conventional techniques, i.e. P-waves, R-waves, etc. are identified. The set-up unit then labels the signal vectors that had been simultaneously detected by the implanted device based on the identity derived from the ECG. In other words, all signal vectors detected during P-waves are labeled as P-wave signal vectors; all signal vectors detected during R-waves are labeled as R-wave signal vectors; and so on. Labeling is achieved by storing appropriate identification values along with the signal vector data already stored in memory. Note that not all signal vectors are labeled. Only signal vectors that correspond to events detected within the ECG are labeled. Signal vectors detected during quiet periods between electrically significant events are not labeled since no corresponding event is detected in the ECG. Likewise, signal vectors corresponding to electrical noise are not labeled.

The set-up unit then processes the labeled signal vectors, at step 416, to generate unique classification zones for the various event types. This involves determining a geometric range for each classification zone, which will be described with reference to FIG. 11. Once the classification zones have been determined, data specifying the zones is assembled into the classification zone data packet along with a list of the events of interest and the optimal electrode combinations and transmitted to the implanted device, at step 418. The physician then controls the implanted device to commence identifying cardiac events (step 419) using the new classification zones in accordance with the method of FIG. 9. If a previous set of classification zones has already been programmed into the implanted device, the new set replaces the older set. Although not shown in FIG. 11, preferably, the physician verifies that the implanted device is correctly identifying cardiac events. This may be achieved by controlling the external programmer to receive and process surface ECG signals and controlling the implanted device to begin transmitting IEGM signals, with the cardiac events (identified using the new classification zones) labeled therein. The external programmer then identifies the events based on the surface ECG signals and compares with the event-identification labels provided by the implanted device to verify correct operation of the device. If the implanted device is not correctly identifying cardiac events using the new zone classifications, appropriate steps may be taken such as repeating the steps of FIG. 11 to generate a new set of classification zones or reloading default classification zones originally programmed into the implanted device.

Figure 10:
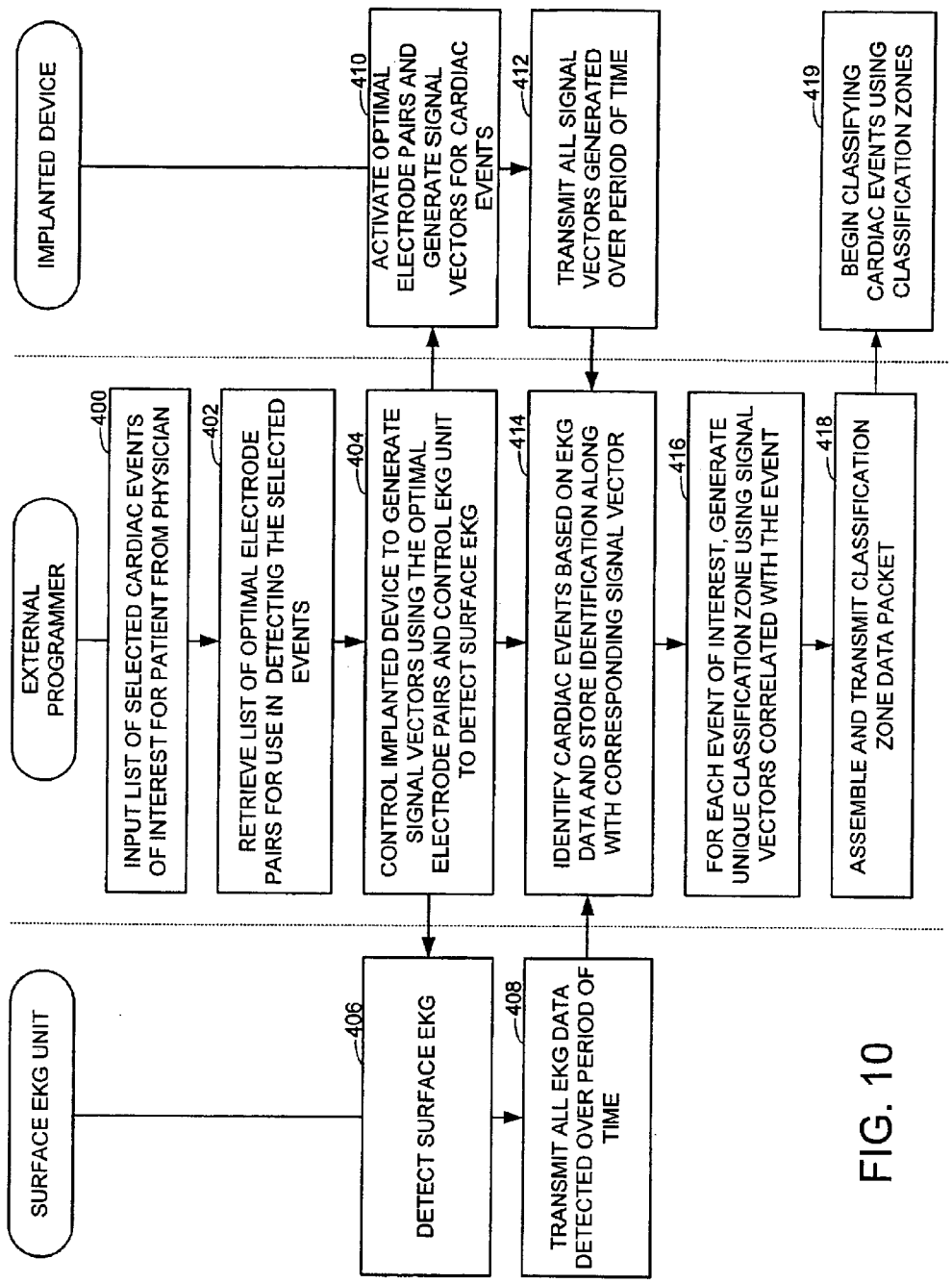
FIG. 10 illustrates an exemplary technique performed by the set-up unit of the programmer of FIG. 3 for generating the set of classification zones.
Figure 11:
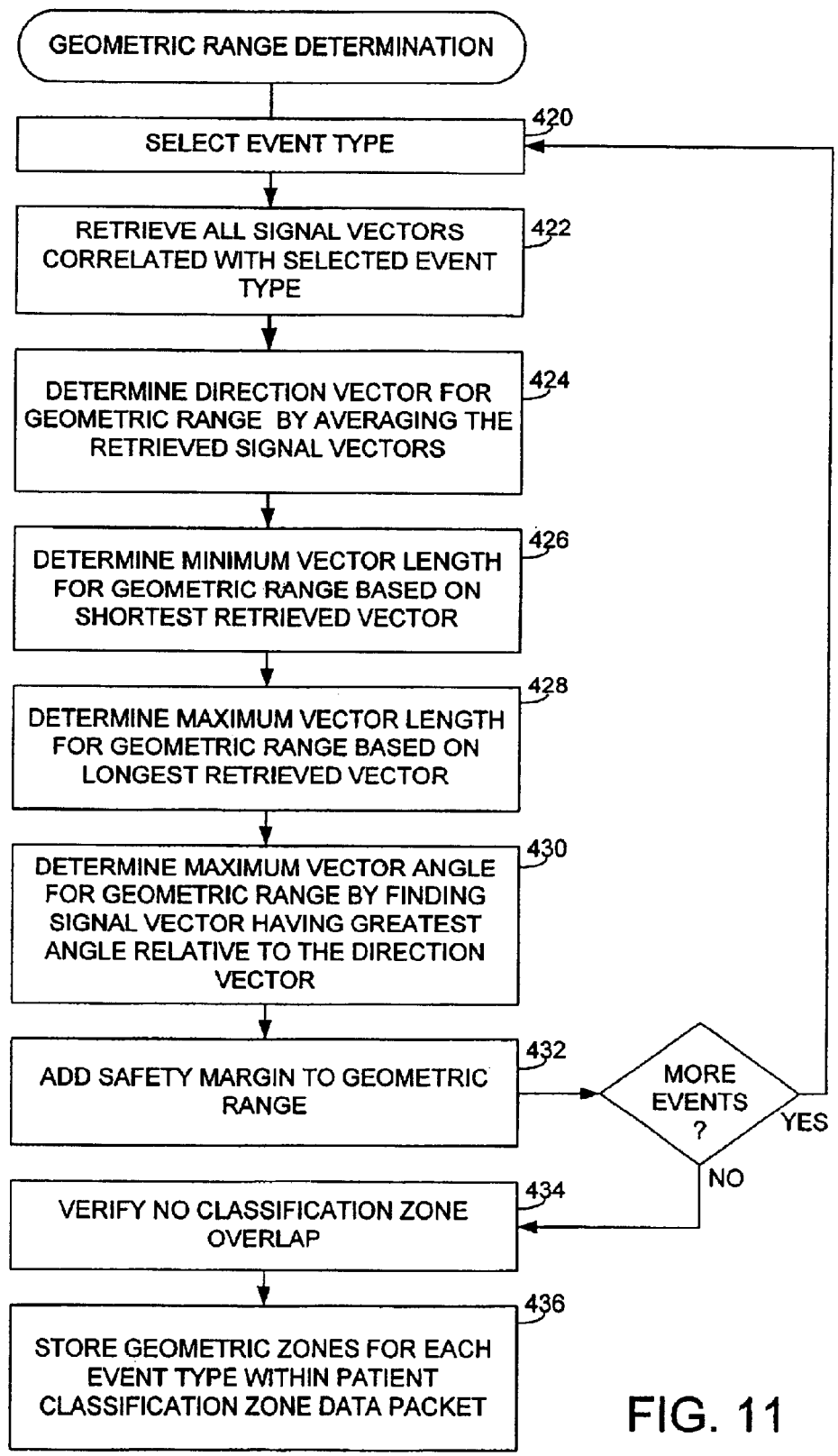
FIG. 11 illustrates an exemplary technique performed by the set-up unit of the programmer of FIG. 3 for determining geometric ranges for the classification zones of FIG. 10.

Referring now to FIG. 11, the method by which the geometric ranges of the classification zones are derived within step 416 of FIG. 10 will now be described. At step 420, the set-up unit selects the first event from the list of events of interest originally input at step 400 of FIG. 10. In this example, it will be assumed that the first event is a P-wave. At step 422, all signal vectors that had been labeled (at step 414 of FIG. 10) as corresponding to P-waves are then retrieved from memory. The signal vectors are then averaged together at step 424 to determine the direction vector for the P-wave classification zone. At steps 426 and 428, the minimum and maximum vector lengths for the P-wave classification zone are generated by identifying, respectively, the shortest and longest individual P-wave signal vectors. At step 430, the maximum vector angle for the zone is determined. These geometrical features are shown in FIG. 8 and the mathematical calculations for determining the geometrical features are described above in connection with the descriptions of FIG. 8.

Hence, steps 422–430 operate to generate a P-wave classification zone based on the cluster of P-wave signal vectors generated by the implanted device during the steps 410 and 412 of FIG. 10. The size of the classification zone is just sufficient to enclose all of the P-wave signal vectors. However, additional valid P-wave signal vectors may fall slightly outside the classification zone. At step 434, the size of the classification zone is expanded to thereby provide a safety margin sufficient to ensure that additional valid P-waves also fall within the classification zone and hence will be properly classified as P-waves. The classification zone is expanded by decreasing the minimum vector length, increasing the maximum vector length and increasing the maximum vector angle, by predetermined percentages, perhaps 20–30%. Preferably, the precise percentage amount of the safety margin is determined via routine experimentation, and may vary from patient to patient. In the alternative, classification zones may be "trimmed" to tighter boundaries, depending on their clustering relative to one another, by using statistical 3-sigma or 4-sigma values for $\Theta_i$, $I_i$, and $L_i$ instead of safety margins.

The process of steps 420–432 are repeated for each additional selected event type to thereby generate classification zones for those event types as well. In the exemplary technique of FIG. 11, each classification zone is specified as a multidimensional truncated zone. However, as noted above, in other examples, each zone has a different geometric shape and so different calculation techniques are employed within steps 420–432 for each event type. In any case, once classification zones have been generated for all selected event types, the set-up unit verifies, at step 434, that none of the classification zones overlap, then stores the resulting geometric zones at step 436 within the patient classification zone data packet. In the extremely unlikely event that any of the classification zones overlap, then a signal vector lying within the overlapping region would not be properly classifiable. So if any overlap is detected, a warning signal is generated (and an appropriate screen is presented on the display screen of the external programmer) to alert the physical of the problem, which might be correctable by selecting a different combination of electrode pairs and repeating the steps of FIGS. 10 and 11 to generate new classification zones based on the new electrode combinations. Again, the zones are examined to verify that no overlap occurs.

In an alternative technique, rather than retrieving a list of optimal electrode combinations at step 402 of FIG. 10, the set-up unit initially controls the implanted device to activate all electrode pairs and to generate signal vectors based on all electrode pairs. The set-up unit then generates classification zones using the method of FIG. 11 for all or selected combinations of the electrodes pairs. The set-up unit then selects the combination of electrode pairs that provides the greatest separation of classification zones to thereby provide for the most reliable event classification while also eliminating any overlap problems.

Event Sequence Classification Method

Figure 12:
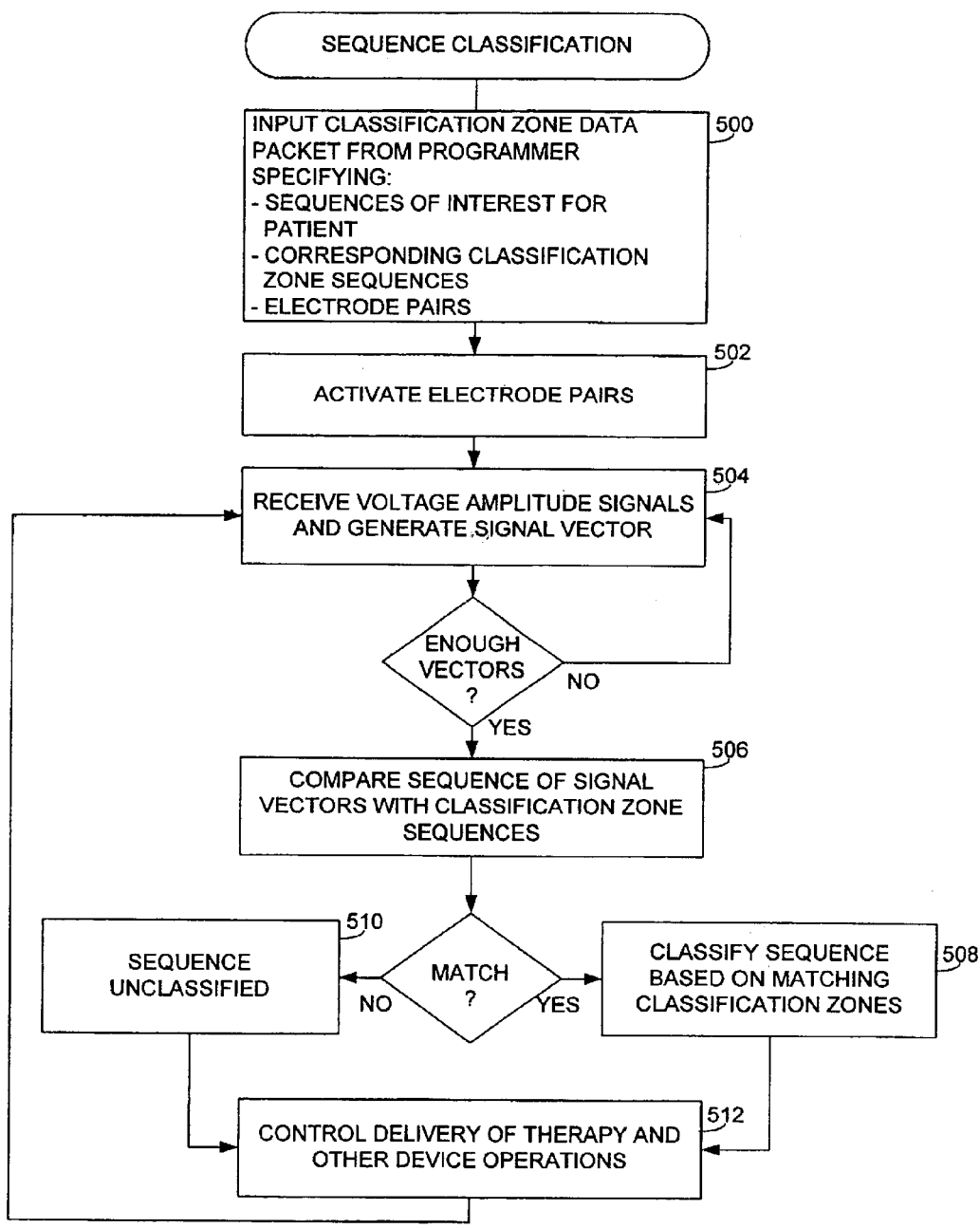
FIG. 12 illustrates a second exemplary technique performed by the vector-based cardiac event detection unit of FIG. 2 for classifying a sequence of electrical events sensed in the heart using sequences of signal vectors and pre-determined classification zones.

FIG. 12 illustrates an alternative method wherein entire sequences of events are detected rather than individual events. The sequence-based method is similar to the single event-based method of FIG. 9 and only pertinent differences will be described in detail. At step 500, the implanted device inputs a sequence-based zone classification packet from the external programmer that specifies: 1) sequences of events of interest for the particular patient; 2) corresponding sequences of classification zones; and 3) a set of electrode pair combinations to be used by the device to sense signal vectors for comparison against the classification zones. Exemplary sequences include a normal sinus beat or PVC. In general, each and every event sequence that the implanted device must detect in order to administer therapy is specified. Additionally, events of purely diagnostic interest may be specified.

At step 502, the event detection unit controls the implanted device to activate sense amplifiers associated with the electrode pairs specified in the sequence-based zone classification packet and, at step 504, begins receiving voltage amplitude signals from the pairs of electrodes. A sequence of signal vectors is generated from the sampled voltages and, once a sufficient number of signal vectors are detected then, at step 506, the sequence of signal vectors is compared against the classification zone sequences. To determine when a sufficient number of signal vectors have been detected, the device may employ a timer or a counter for counting the number of signal vectors detected. Also at step 506, the sequence of signal vectors is compared with the set of classification zone sequences to classify the sequence of events. The comparison at step 506 is performed by sequentially comparing each set of classification zone sequences with the sequence of signal vectors until a match is found. If the sequence of signal vectors matches one of the classification zone sequences, the electrical event in the heart represented by the sequence of signal vectors is classified based on the zone sequence at step 508. Thus, if the sequence of signal vectors matched the normal sinus beat zone sequence, the sequence of events is classified as a normal sinus beat and so on. If the sequence of signal vectors does not match any of the classification zone sequences, the electrical event is deemed to be unclassified, at step 510, and diagnostic data is stored identifying the unclassified event. In any case, step 512 is then performed wherein the event detection unit forwards the results of the classification process to the microcontroller for use in controlling operations of the implanted device to, for example, administer cardiac pacing or defibrillation therapy to the patient or to store diagnostic information. Processing then immediately returns to step 504 to sense and classify the next event.

Figure 9:
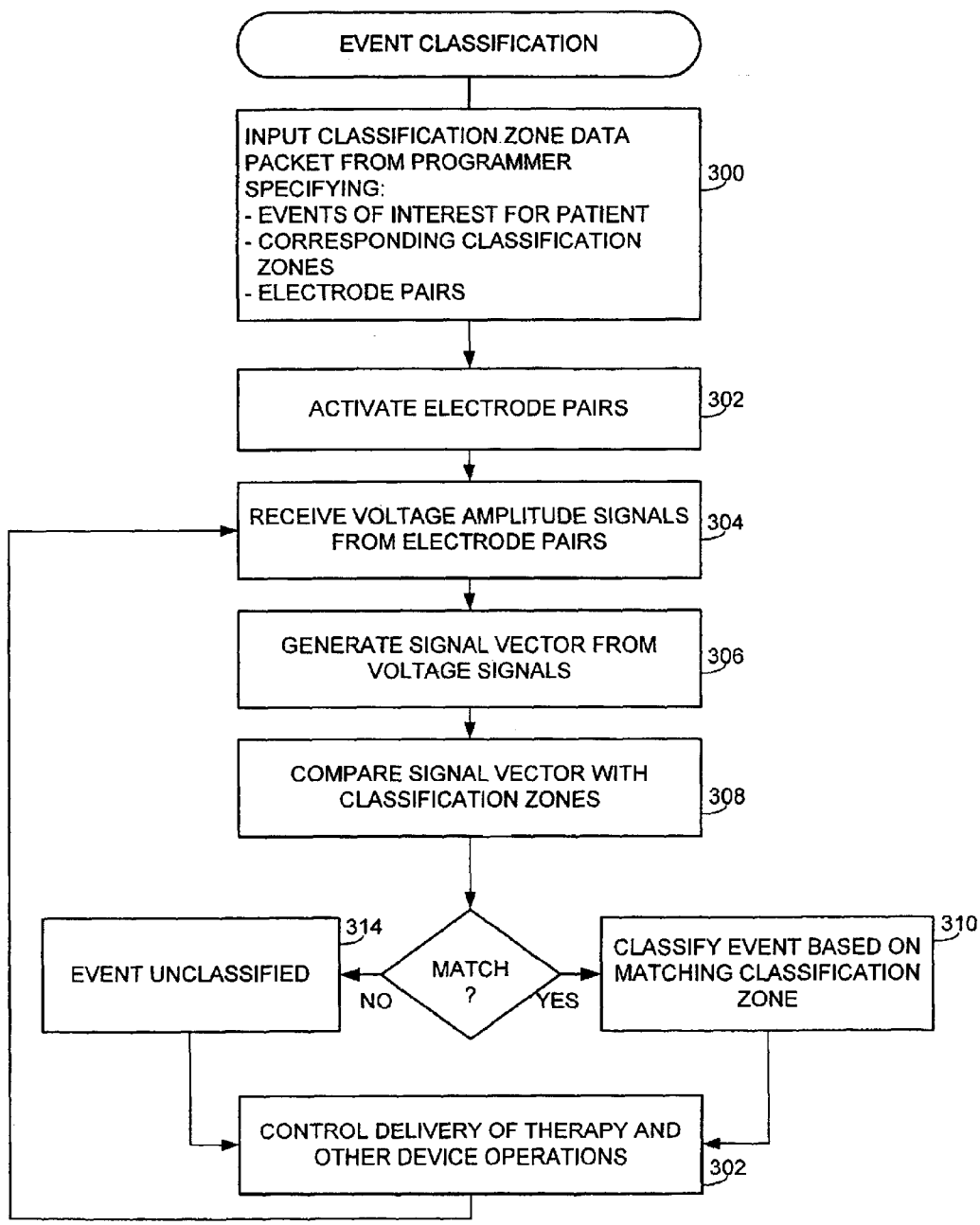
FIG. 9 illustrates a first exemplary technique performed by the vector-based cardiac event detection unit of FIG. 2 for classifying individual electrical events sensed in the heart using signal vectors and pre-determined classification zones.

Thus FIG. 12 sets forth a sequence-based detection technique similar to the single event-base detection technique of FIG. 9. Depending upon the programming of the system, both techniques may be implanted together, thus providing two-levels of event detection. In addition to detecting events such as P-waves, PACs, etc, the technique may also be exploited to detect atrial fibrillation, ventricular fibrillation or other such dysrhythmias. In general, any of a wide variety of cardiac electrical events or patterns occurring within the patient may be detected so long as the events can be represented by appropriate classification zones or zone sequences. Routine experimentation may be employed to identify and characterize such events or patterns and to generate the appropriate classification zones or zone sequences.

What have been described are various techniques for classifying cardiac electrical events and for adjusting or administering therapy based thereon. In general, the embodiments described herein are merely illustrative of the invention and should not be construed as limiting the scope of the invention, which is to be interpreted in accordance with the claims that follow.

What is claimed is:

1. In an implantable cardiac stimulation device for implant within a patient wherein the device has multiple electrodes, a method for detecting cardiac electrical events comprising:
   inputting a data packet representative of a set of vector classification zones pertinent to a particular implantable cardiac stimulation device;
   sensing electrical signals from selected combinations of the electrodes;
   calculating a vector representative of the electrical signals; and
   comparing the vector with the set of vector classification zones, each representative of a different electrical event within the heart of the patient, to classify the electrical event.

2. The method of claim 1 wherein the electrical events include one or more of P-waves, R-waves, T-waves, A-waves, V-waves, premature ventricular contraction (PVCs), premature atrial contraction (PACs), atrial fibrillation (A-fib) events and ventricular fibrillation (V-fib) events and wherein the step of comparing the vector with a set of predetermined vector classification zones includes the step of comparing the vector with zones representative of one or more of P-waves, R-waves, T-waves, A-waves, V-waves, PVCs and PACs to classify the event as either a P-wave, R-wave, T-wave, A-wave, V-wave, PVC, PACs, an A-fib event or a V-fib event.

3. The method of claim 1 wherein the electrodes include one or more of an atrial tip electrode (A-tip), an atrial ring electrode (A-ring), a ventricular tip electrode (V-tip), a ventricular ring electrode (V-ring), a coil, and a device can and the step of sensing electrical signals from various combinations of the electrodes includes the step of sensing voltage signals between two or more of the electrodes.

4. The method of claim 3 wherein the step of sensing voltage signals between two or more of the electrodes includes the step of sensing one or more of an A-tip to device can voltage, an A-tip to coil voltage, an A-tip to V-ring voltage, an A-tip to V-tip voltage, an A-tip to A-ring voltage, an A-ring to device can voltage, an A-ring to coil voltage, an A-ring to V-ring voltage, an A-ring to V-tip voltage, a V-tip to device can voltage, a V-tip to coil voltage, a V-tip to V-ring voltage, a V-ring to can voltage, a V-ring to coil voltage, and coil to device can voltage.

5. The method of claim 4 wherein the step of calculating a vector representative of the electrical signals includes the step of calculating one or more components of a vector $A=[a_1, \ldots, a_{15}]$ wherein $a_1, \ldots, a_{15}$ represent, respectively, the A-tip to device can voltage, the A-tip to coil voltage, the A-tip to V-ring voltage, the A-tip to V-tip voltage, the A-tip to A-ring voltage, the A-ring to device can voltage, the A-ring to coil voltage, the A-ring to V-ring voltage, the A-ring to V-tip voltage, the V-tip to device can voltage, the V-tip to coil voltage, the V-tip to V-ring voltage, the V-ring to can voltage, the V-ring to coil voltage, and the coil to device can voltage.

6. The method of claim 1 further including the step of controlling the delivery of therapy based on the classification of the event.

7. The method of claim 1 further including the steps of:
   identifying events that do not correspond to any of the predetermined vector classification zones; and
   storing diagnostic information representative of the events that do not correspond to any of the predetermined vector classification zones.

8. The method of claim 7 wherein the step of storing diagnostic information includes the step of storing values representative of the vectors of the events that do not match any of the vector classification zones.

9. The method of claim 1 wherein the data packet comprises vector classification zones corresponding to one or more of P-waves, R-waves, A-waves, V-waves, and T-waves.

10. The method of claim 1 wherein the step of comparing the vector with a set of predetermined vector classification zones includes the step of:
    comparing a sequence of vectors with a sequence of vector classification zones, each representative of a different sequence of electrical events within the heart of the patient, to classify the electrical event.

11. The method of claim 10 wherein the data packet comprises vector classification zones corresponding to one or more of sinus beats, premature ventricular contractions (PVCs), premature atrial contraction (PACs), atrial fibrillation events and ventricular fibrillation events.

12. The method of claim 1 wherein the predetermined vector classification zone is a multidimensional truncated cone.

13. The method of claim 1 wherein the predetermined vector classification zone is represented by a direction vector, a maximum angle from the vector, a minimum vector length and a maximum vector length.

14. The method of claim 1 further including the initial steps of:
    determining the vector classification zones for the particular patient in which the device is implanted; and
    storing the vector classification zones within the implantable device for subsequent use with the patient.

15. In an implantable cardiac stimulation device for implant within a patient wherein the device has multiple electrodes, a method for detecting cardiac electrical events comprising:
    determining vector classification zones, each representative of a different electrical event within the heart of a particular patient in which the device is implanted;

storing the vector classification zones within the implantable device for subsequent use with the particular patient;

sensing electrical signals from selected combinations of the electrodes;

calculating a vector representative of the electrical signals; and comparing the vector with the stored set of vector classification zones to classify the electrical event, wherein determining the vector classification zones comprises sensing electrical signals from the selected combination of electrodes corresponding to electrical events and calculating signal vectors for the electrical events;

identifying the electrical events based on ECG signals; and correlating the signal vectors with the corresponding electrical events and, for each type of electrical event, calculating the characteristics of the classification zone for the event based on all signal vectors correlated with the event.

16. The method of claim 15:
wherein the vector classification zones are each represented by a direction vector and geometric range; and
wherein the step of calculating the characteristics of the classification zone includes the step of calculating the direction vector and the geometric range for the classification zone based on the vectors correlated with the event.

17. The method of claim 16 wherein the step of calculating the geometric range includes the step of adding a safety margin to the geometric range.

18. The method of claim 16:
wherein each geometric range is represented by a maximum angle relative to the direction vector, a minimum vector length and a maximum vector length; and
wherein the step of calculating the geometric range includes the step of calculating the maximum angle, minimum length and maximum length for the classification zone based on the vectors correlated with the event.

19. The method of claim 15 wherein the step of calculating the characteristics of the classification zone includes the step of averaging the vectors correlated with the event.

20. The method of claim 19 wherein, if $(a_{1,1}, a_{1,2}, \ldots, a_{1,m})$, $(a_{2,1}, a_{2,2}, \ldots, a_{2,m})$, $\ldots$, $(a_{n,1}, a_{n,2}, \ldots, a_{n,m})$ represent n signal vectors generated from m electrode pairs, then the step of averaging the signal vectors includes the step of calculating:

$$\dot{\alpha} = (\alpha_1, \alpha_2, \ldots, \alpha_m)$$
$$= [(a_{1,1} + a_{2,1} + \ldots + a_{n,1})/n,$$
$$(a_{1,2} + a_{2,2} + \ldots + a_{n,2})/n, \ldots, (a_{1,m} + a_{2,m} + \ldots + a_{n,m})/n].$$

21. The method of claim 18 wherein the steps of calculating the minimum and maximum lengths include the steps of calculating the length of individual signal vectors and selecting the signal vectors having, respectively, the shortest and longest lengths.

22. The method of claim 18 wherein the step of calculating the maximum angle include the steps of calculating the angles between each of the individual signal vectors and the direction vector and selecting the largest angle.

23. The method of claim 18 wherein the step of calculating the angles between each of the individual signal vectors and the direction vector angle includes the step of calculating $$\Theta = \cos^{-1}[(a_i \cdot \dot{\alpha})/(\|a_i\|\|\dot{\alpha}\|)]$$

wherein $a_i$ represents the sensed vector and $\dot{\alpha}$ represents the direction vector.

24. The method of claim 23 wherein the predetermined vector classification zone is represented by $$Z_i = \{\dot{\alpha}_i, \Theta_i, I_i, L_i\}$$

where $Z_i$ is a classification zone and $\dot{\alpha}_i, \Theta_i, I_i,$ and $L_i$ represent the direction vector, maximum angle, minimum length, and maximum length, respectively.

25. The method of claim 24 wherein the step of comparing a vector with a set of predetermined vector classification zones to classify the electrical event includes the step of determining whether the vector is within the vector classification zone.

26. The method of claim 25 wherein the step of determining whether the vector is within the vector classification zone includes the steps of:

determining whether $I_i <= \|A\| <= L_i$; and determining whether $(A \cdot \dot{\alpha})/(\|A\|\|\dot{\alpha}\|) <= \cos \Theta_i$;

wherein $Z_i = \{\dot{\alpha}_i, \Theta_i, I_i, L_i\}$ represents the classification zone and a represents the vector.

27. In an implantable cardiac stimulation device having multiple electrodes for implant within a patient, a system for detecting cardiac electrical events comprising:

a set of sense amplifiers operative to sense voltages between selected combinations of the electrodes;

memory operative to store a data packet representative of a set of vector classification zones pertinent to a particular implantable cardiac stimulation device; and a vector-based cardiac event detection unit operative to identify cardiac electrical events based on the voltages sensed between the selected combinations of electrodes by calculating a vector representative of the electrical signals and comparing the vector with the stored vector classification zones, wherein each vector classification zone is representative of a different electrical event.

28. In an implantable cardiac stimulation device for implant within a patient wherein the device has multiple electrodes, a system for detecting cardiac electrical events comprising:

means for inputting a data packet representative of a set of vector classification zones pertinent to a particular implantable cardiac stimulation device;

means for sensing electrical signals from selected combinations of the electrodes; and means for identifying cardiac electrical events based on the voltages sensed between the selected combinations of electrodes by calculating a vector representative of the electrical signals and comparing the vector with the set of vector classification zones, each representative of a different electrical event within the heart of the patient.

* * * * *